(12) United States Patent
Holland

(10) Patent No.: US 6,607,483 B1
(45) Date of Patent: Aug. 19, 2003

(54) METHOD AND APPARATUS FOR HEALTH AND FITNESS FEEDBACK

(75) Inventor: Randall Allen Holland, Nashville, TN (US)

(73) Assignee: Fitness Holdings, LLC, Nashville, TN (US)

(*) Notice: Subject to any disclaimer, the term of this patent is extended or adjusted under 35 U.S.C. 154(b) by 0 days.

(21) Appl. No.: 09/828,578

(22) Filed: Apr. 5, 2001

Related U.S. Application Data

(60) Provisional application No. 60/194,819, filed on Apr. 5, 2000.

(51) Int. Cl.[7] .............................................. A61B 5/00
(52) U.S. Cl. ............................. 600/300; 128/921; 482/8
(58) Field of Search ................................ 600/300–301, 600/481, 500, 529–532; 128/903–904, 920–925; 705/2–4; 702/19; 482/8–9

(56) References Cited

U.S. PATENT DOCUMENTS

| | | | | |
|---|---|---|---|---|
| 4,951,197 A | * | 8/1990 | Mellinger | 600/300 |
| 5,839,901 A | * | 11/1998 | Karkanen | 434/127 |
| 5,954,640 A | * | 9/1999 | Szabo | 600/300 |
| 6,478,736 B1 | * | 11/2002 | Mault | 600/300 |
| 6,497,638 B1 | * | 12/2002 | Shea | 482/8 |

OTHER PUBLICATIONS

Joe Green, "Online Resources Good for Health", Jul. 13, 1999, Chicago Sun–Times.*
www.healthcalc.net/software.htm.*
www.healthcalc.net/products.htm.*

* cited by examiner

Primary Examiner—Max F. Hindenburg
Assistant Examiner—Michael Astorino
(74) Attorney, Agent, or Firm—David B Pieper; Phillip E. Walker

(57) ABSTRACT

A fitness monitoring system and method for accepting, assessing, maintaining, training, monitoring, and providing direct feedback for individuals in a fitness program for improved results. The method provides feedback on a member of a fitness program utilizing a computer system database and includes performing an initial assessment of the fitness characteristics of a member to gather initial assessment information, recording the initial assessment information in the computer system database, performing a final assessment of the fitness characteristics of a member to gather initial assessment information, recording the final assessment information in the computer system database, and calculating the changes in the health characteristics of the member stored in the database between the initial and final assessments. An alternative method monitors the health characteristics of the member for multiple time intervals and calculates the changes in the health characteristics of the member stored in the database between the two time intervals.

38 Claims, 22 Drawing Sheets

— 700

| You Can Access All Member-Specific Records from this Page |

Please Select Trainer: _____ —702
Please Select Workout Time _____—704          706
Choose Member: _____

Click on One of the Buttons Below to View or Add Information:

| Enter Daily Data | View Weekly Results | End of Boot Results | Print Maintenance Guide |

—708    —710    —712    —714

720
To Compare Changes in Specific Assessment Dates, Choose Dates Below:

| First Date | _____ | View Change |
| Second Date | _____ | |

| Select New Member |    718  716          Close
—722                          724

Member 1002   Date 1012 1004 9/20/00

Age 1006   You Must Select Assessment Type:   Assessor 1010
Sex Male   | Initial Boot | Other (Mid-Term or Non-Boot) |
Weight
1008  1014  1016

Resting Heart Rat 1018

Bottom of Target Range  62.00%   Heart Rate
Middle of Target Range  70.00%   Heart Rate
Top of Target Range  78.00%   Heart Rate New Record Find Record Print Assessments Main Menu

Member   Date 9/20/00

Age   You Must Select Assessment Type:   Assessor
Sex Male   | Initial Boot | Other (Mid-Term or Non-Boot) |
Weight

| 7-Site Jackson, Pollack and Ward: | | Tape Measurements | |
|---|---|---|---|
| Chest | 0 —1102 | Shoulders: | 0 —1118 |
| Axilla | 0 —1104 | Chest: | 0.00 —1120 |
| Triceps | 0 —1106 | Waist: | 0.00 —1122 |
| Subscapula | 0 —1108 | Hips: | 0.00 —1124 |
| Abdomen | 0 —1110 | Upper Arm Right: | 0.00 —1126 |
| Suprailium | 0 —1112 | Upper Arm Left: | 0.00 —1128 |
| Thigh | 0 —1114 | Thigh Right: | 0.00 —1130 |
| Total: | 0.0 —1116 | Thigh Left: | 0.00 —1132 |

Calculate —1134
Body Fat

New Record

Find Record

Print Assessments

Main Menu

| | | | | |
|---|---|---|---|---|
| Member | | | Date | 9/20/00 |

Age ☐  
Sex [Male]   You Must Select Assessment Type:   Assessor _____
Weight ☐   Initial Boot ☐   Other (Mid-Term or Non-Boot) ■

```
           1202   1204   1206      1208
         Weight  Body Fat %  Lean Wt  Fat/Fluid Wt
                                            1212
Now:      ☐      ☐       ☐       ☐
                                          ┌─────┐
Predicted Fluid  0.0 —1210                │Water│
Loss:                  —1216              │Weight│
                —1214                      └─────┘
Goal:     ☐      ☐       ☐       ☐
                    —1215    —1217
Weeks:    8 —1218

Calculated Weekly
Change:
```

New Record ✎

Find Record 🔍

Print Assessments 🖶

Main Menu ☞

| This List Contains Guidelines Regarding "Typical" Water Weigth for Males and Females, based only on Body Fat% |||
| --- | --- | --- |
| Body Fat % | Male Water Wt | Female Water Wt |
| 10% | 0.0 | 0.0 |
| 11% | 0.0 | 0.0 |
| 12% | 0.0 | 0.0 |
| 13% | 0.0 | 0.0 |
| 14% | 0.5 | 0.0 |
| 15% | 0.5 | 0.0 |
| 16% | 1.0 | 0.0 |
| 17% | 1.0 | 0.0 |
| 18% | 2.0 | 0.5 |
| 19% | 3.0 | 0.5 |
| 20% | 4.0 | 1.0 |
| 21% | 5.0 | 1.0 |
| 22% | 6.0 | 2.0 |
| 23% | 6.0 | 2.0 |
| 24% | 6.0 | 3.0 |
| 25% | 6.0 | 3.0 |
| 26% | 7.0 | 4.0 |
| 27% | 8.0 | 5.0 |
| 28% | 9.0 | 6.0 |
| 29% | 10.0 | 6.0 |
| 30% | 11.0 | 6.0 |
| 31% | 12.0 | 7.0 |
| 32% | 13.0 | 8.0 |
| 33% | 14.0 | 9.0 |
| 34% | 15.0 | 10.0 |
| 35% | 16.0 | 11.0 |
| 36% | 17.0 | 12.0 |
| 37% | 18.0 | 13.0 |
| 38% | 19.0 | 14.0 |

*In General, add 1/2 lb. for a high sodium diet. Also add 1/2 lb. for if member drinks less than half the recommended amount of water.

Close

| Member | | Date | 9/20/00 |

Age  
Sex Male  
Weight

You Must Select Assessment Type:  
Initial Boot ☐   Other (Mid-Term or Non-Boot) ■

Assessor

Click for Metabolism —1402
Sum of Predicted Metabolism —1404
- #1's  [0] —1406
- #2's  [0] —1408
- #3's  [0] —1410
- #4's  [0] —1412
- #5's  [0] —1414
- #6's  [0] —1416
- Total (23) [0] —1418

—1420 Calculate

Metabolism [ ] —1422

New Record  
Find Record  
Print Assessments  
Main Menu

Energy Level Rating Chart — 1500

| HOUR | |
|---|---|
| 9:00 PM | |
| 10:00 PM | |
| 11:00 PM | |
| 12:00 AM | |
| 1:00 AM | |
| 2:00 AM | |
| 3:00 AM | |
| 4:00 AM | |
| 5:00 AM | |
| 6:00 AM | |
| 7:00 AM | |
| 8:00 AM | |
| 9:00 AM | |
| 10:00 AM | |
| 11:00 AM | |
| 12:00 PM | |
| 1:00 PM | |
| 2:00 PM | |
| 3:00 PM | |
| 4:00 PM | |
| 5:00 PM | |
| 6:00 PM | |
| 7:00 PM | |
| 8:00 PM | |

For each hour of your day, find the activity below that coincides with your typical routine for each hour and place that number in the corresponding time slot. Place a "0" next to the hour that coincides with your typical cardio time

RATING

1 SLEEP

2 LIGHT — Cooking  Driving  Talking  Paperwork
          Typing   Reading  Sitting  Studying 3 MODERATE — Doctor   Nurse    Labwork    Teaching
             Walking  Talking  Housework  Sales Clerk 4 HEAVY — Strenuous Labor

5 BOOT 3 STRENGTH TRAINING

6 BOOT 5 STRENGTH TRAINING

TOTAL # 1's: _____   TOTAL # 4's: _____

TOTAL # 2's: _____   TOTAL # 5's: _____

TOTAL # 3's: _____   TOTAL # 6's: _____

1502

Member [ ] Date [ 9/20/00 ]
Age [ ]    You Must Select Assessment Type:    Assessor [ ]
Sex [ Male ]   [ Initial Boot ☑ ]  [ Other (Mid-Term or Non-Boot) ■ ]
Weight [ ]

Please Answer the Following Questions Honestly: ←—1602      1604

1. I have problems with weight:    ◉ My Whole Life  ◉ Most of My Life  ◉ In Recent Years  ◉ Never
2. I weight train strenuously on a regular basis:  ◉ 0 Days/Week  ◉ 1-2 Days/Week  ◉ 3+ Days/Week
3. When I try, I am: [ ◉ Unsuccessful  ◉ Somewhat Successful  ◉ Successful  ◉ Very Successful ] in losing weight.
4. Check if you have been on a High Protein / Carb Depletion Diet  ☐ ←—1608   1606
   (Atkins, Sugar Busters, etc)
   # of Months on Diet        [ 0 ] ←—1610
   # of Pounds Lost           [ 0 ] ←—1612         [ Calculate CAMS ] —1618
   # of Months Since Diet     [ 0 ] ←—1614
   # of Pounds Gained Since Die [ 0 ] ←—1616       CAMS (% of PAMS) [ ]

New Record • Find Record • Print Assessments • Main Menu

Member [ ] Date [ 9/20/00 ]
Age [ ]    You Must Select Assessment Type:    Assessor [ ]
Sex [ Male ]   [ Initial Boot ☐ ]  [ Other (Mid-Term or Non-Boot) ■ ]
Weight [ ]

Daily Diet: ←—1702  —1704                                       —1718
[ Suggest Diet ] [ ]  —1706             [ Click to Calculate Water and Diet ]
Choose Diet: [ ] —1708
                                        1720 { Protein (g): [ ]
PAMS/CAMS: —1710                           Carbs (g): [ ]
                                        1722 { Fat (g): [ ]
PAMS: [ 10.0% ]   Click to Increase %         Water (lts): [ ]
CAMS: [ ]         (Password Required)         Water (oz): [ ]
% Daily Metabolism: [ 100.0% ] —1714  1724
Total Daily Calories: [ ] —1716         Cardio Requirement:
                                        Total Weekly Cardio: [ ]
                                        5 Days: [ ]   6 Days: [ ]

1700    1712                                       —1726

New Record • Find Record • Print Assessments • Main Menu

FIG. 18

Members

Last Name [Smith] — 2002
First Name [John] — 2004

*Check This Box if Person is only a Prospect* ☐ — 2006

<u>Please Use the Aphelion "Barcode #" as the Member ID.</u>
<u>If Member is a Prospect, Use "P","plus phone # as ID.</u>

Member ID [1] — 2008

Member Since: [ ] — 2010

Reffered By: [ ] — 2012

Home Phone #: (615) - — 2020
Work Phone #: (615) - — 2022

Address [ ] ⎤
Address 2: [ ] ⎦ — 2014
City [ ] — 2016
State [ ] — 2018
Zip Code [ ] — 2020

Please Enter Current Training Program: — 2024, 2026

Trainer [No] — 2028
Program [None] — 2028
Time [ ]

[Click to Locate a Member] — 2030

[Add New Member] — 2034
[Begin Assessment] — 2032
[Main Menu] — 2036

MEMBER REFERRALS:

| Last Name | First Name | Referred By: | Prospect | Home # | Work # | Address | City | State | Zip Code |
|---|---|---|---|---|---|---|---|---|---|
| Burksdale | Julia | BETSY MAYTON | ☑ | (615) 665-13 | | 3904 Wayland Drive | Nashville | TN | 37215 |
| Burnet | Pam | BETSY MAYTON | ☑ | (615) 371-87 | | 5440 Granny White Pike | Nashville | TN | 37027 |
| Edwards | Karen | BETSY MAYTON | ☑ | (615) 386-36 | | 3921 Caylor Drive | Nashville | TN | 37215 |
| Elliston | Mary De | BETSY MAYTON | ☑ | (615) 665-04 | | 45098 Harpeth Hills Drive | Nashville | TN | 37215 |
| Evans | Mary | BETSY MAYTON | ☑ | (615) 244-20 | | 4440 Arden Place | Nashville | TN | 37215 |
| Gibbs | Gayle | BETSY MAYTON | ☑ | (615) 385-11 | | 3700 Sycamore Lane | Nashville | TN | 37215 |
| Gilliam | Sally | BETSY MAYTON | ☑ | (615) 371-16 | | 5305 Cherry Blossom Trail | Nashville | TN | 37215 |
| Neblett | Margaret | BETSY MAYTON | ☑ | (615) 373-26 | | 1126 Tyne Blvd | Nashville | TN | 37220 |
| Ragsdale | Marsha | BETSY MAYTON | ☑ | (615) 297-07 | | 4409 Saper Ave | Nashville | TN | 37204 |
| Tennyson | Di Ann | BETSY MAYTON | ☑ | (615) 373-23 | | 302 Appomat Ox Dr | Brentwood | TN | 37027 |

[Close Form] — 2102

Trainer Schedules

| | Member | Program | Home # | Work # |
|---|---|---|---|---|
| Trainer: ▢—2302 | ▢—2304 | ▢—2308 | ▢—2310 | ▢—2312 |
| Time: ▢ ▢ |  |  |  |  |
| —2306 |  |  |  |  |

Trainer:

Time:

Assessments by Trainer

Trainer:

Member:

Protein %:  Time  Program:

Current:  Goals:

| Date | Assessor: | Weight | Fat % | Lean Wt | Fat Wt | Weight | Lean Wt | Fat % | Fat Wt | Initial Fluid | Weeks of Program | | | | Predicted Weekly Changes | | | |
|------|-----------|--------|-------|---------|--------|--------|---------|-------|--------|---------------|------------------|--|--|--|--------------------------|--|--|--|
| | | | | | | | | | | | | | | | Weight Change | Muscle Buile | Fat Loss | Fat % Loss |
| | | | | | | | | | | | | | | | | | | |
| | | | | | | | | | | | | | | | | | | |

Trainer:

Member:

Protein %:  Time  Program

Current:  Goals:

| Date | Assessor: | Weight | Fat % | Lean Wt | Fat Wt | Weight | Lean Wt | Fat % | Fat Wt | Initial Fluid | Weeks of Program | | | | Predicted Weekly Changes | | | |
|------|-----------|--------|-------|---------|--------|--------|---------|-------|--------|---------------|------------------|--|--|--|--------------------------|--|--|--|
| | | | | | | | | | | | | | | | Weight Change | Muscle Buile | Fat Loss | Fat % Loss |
| | | | | | | | | | | | | | | | | | | |
| | | | | | | | | | | | | | | | | | | |

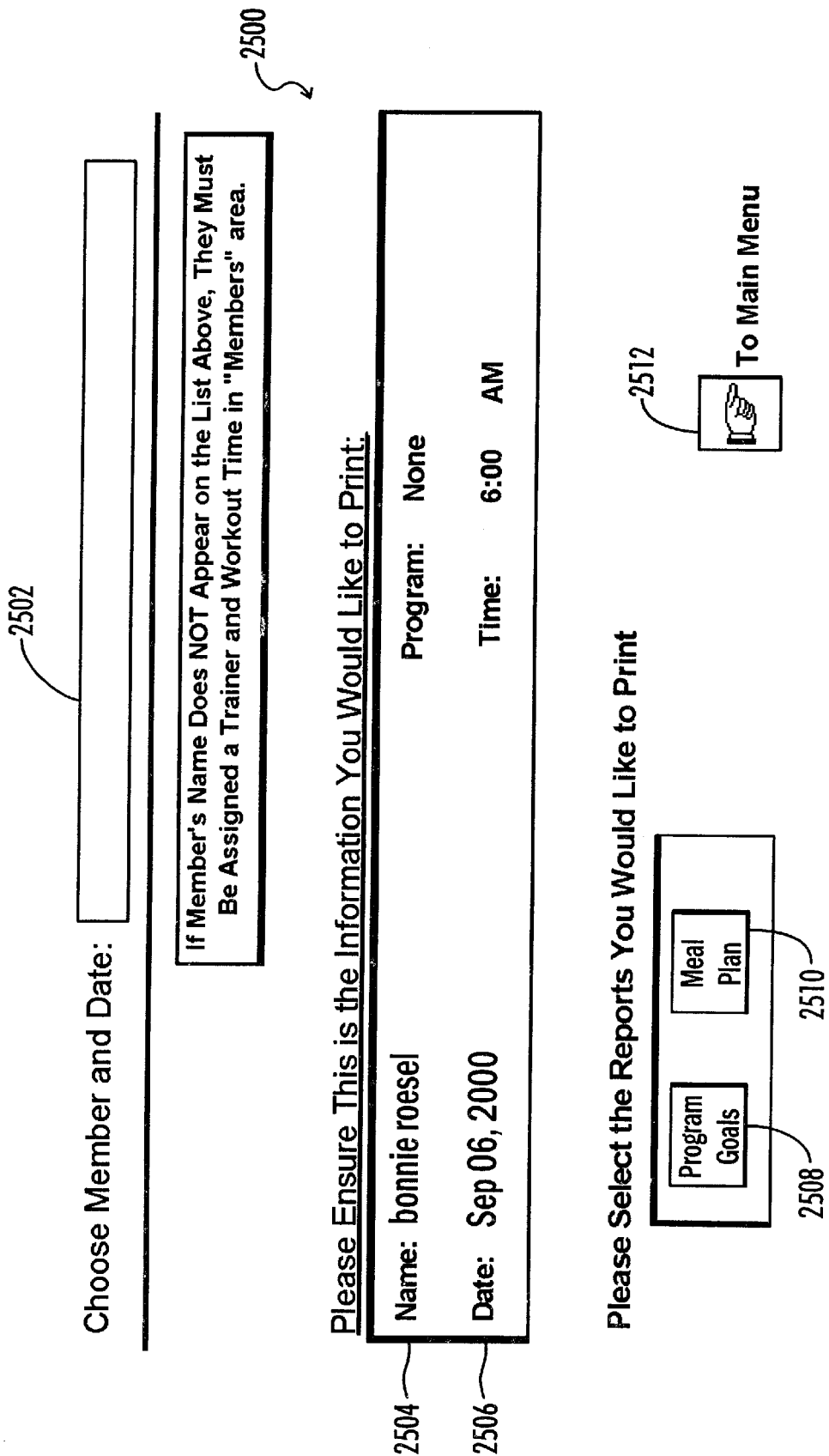

| You Can Use this Form to Generate Letters to Current Clients: |

First, Choose up to 2 Different Programs You Would Like to Send Letters to (for example: Boot 5 and Boot 3)

First Program 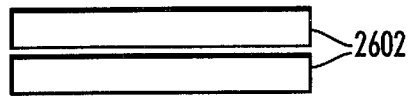
Second Program

— 2602

Next, Select Which Letter You Would Like to Print.

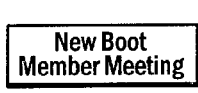 — 2604     — 2606

New Boot Member Meeting    Welcome to New Boot Members

A Letter Should Automatically be Generated for All Members Currently Registered with the Programs Selected. If they are not, please go back through the "Members" form and make sure all current clients are assigned the proper training program.

Main Menu
 — 2608

*FIG. 26*

METHOD AND APPARATUS FOR HEALTH AND FITNESS FEEDBACK

This application claims benefit of co-pending Provisional U.S. Patent Application Ser. No. 60/194,819 filed Apr. 5, 2000, entitled "Method and Apparatus for Health and Fitness Feedback" which is hereby incorporated by reference.

A portion of the disclosure of this patent document contains material which is subject to copyright and trademark protection. The copyright and trademark owner has no objection to the facsimile reproduction by anyone of the patent document or the patent disclosure, as it appears in the Patent Trademark office patent file or records, but otherwise reserves all copyright and trademark rights whatsoever.

BACKGROUND OF THE INVENTION

The present invention relates generally to a fitness monitoring system. More particularly, this invention pertains to a system and method for accepting, assessing, maintaining, training, monitoring, and providing direct feedback for individuals in a fitness program for improved results.

SUMMARY OF THE INVENTION

The present invention teaches a fitness monitoring system and method for accepting, assessing, maintaining, training, monitoring, and providing direct feedback for individuals in a fitness program for improved results. The method provides feedback on a member of a fitness program utilizing a computer system database and includes performing an initial assessment of the fitness characteristics of a member to gather initial assessment information, recording the initial assessment information in the computer system database, performing a final assessment of the fitness characteristics of a member to gather initial assessment information, recording the final assessment information in the computer system database, and calculating the changes in the health characteristics of the member stored in the database between the initial and final assessments.

An alternative method monitors the health characteristics of the member for multiple time intervals and calculates the changes in the health characteristics of the member stored in the database between the two time intervals.

A still further method teaches establishing program goals based on a desired client goal and comparing the health characteristics of the member stored in the database to the program goals stored in the database.

These method utilize multiple data resources for providing this feedback including diet and cardiovascular characteristics; a 7-Site Jackson, Pollock and Ward examination on the chest, axilla, triceps, subscapula, abdome, suprailium, and thigh; tape measurements on the shoulders, chest, waist, hips, upper arm right, upper arm left, thigh right, and thigh left.

Program goals for the clients are established utilizing several factors including establishing a target range for a heart rate of the member for a fitness session; measuring the health characteristics of the member; collecting diet and cardiovascular characteristics; selecting a client diet; predicting fluid loss; predicting member metabolism by activities performed over a time period; calculating CAMS; calculating PAMS; and calculating a cardiovascular requirement for fitness training associated with the client goals.

Other advantages of the present system and method include maintaining membership information and access, trainer information, and fitness program information and providing the ability to generate printed information for results and business contact letters.

These characteristics, the apparatus, and the method are presented in the following detailed discussion.

BRIEF DESCRIPTION OF THE DRAWINGS

FIG. 7 shows the enter new data form.

FIG. 8 shows the daily data form.

FIG. 10 shows the new assessment option and associated heart rate form.

FIG. 11 shows the skin folds measurements section screen.

FIG. 12 shows the goals page.

FIG. 14 shows the predicted metabolism screen.

FIG. 15 shows the predicted metabolism worksheet.

FIG. 16 shows the cams/pams screen.

FIG. 17 shows the diet and cardio screen.

FIG. 18 shows the comments page.

FIG. 20 shows the member form.

FIG. 21 shows the member referrals screen.

FIG. 23 shows the trainer schedules form.

FIG. 24 shows the assessments by trainer form.

FIG. 25 shows the printing goals form.

FIG. 26 shows the generate letters form.

DESCRIPTION OF THE PREFERRED EMBODIMENTS

Figure 1:
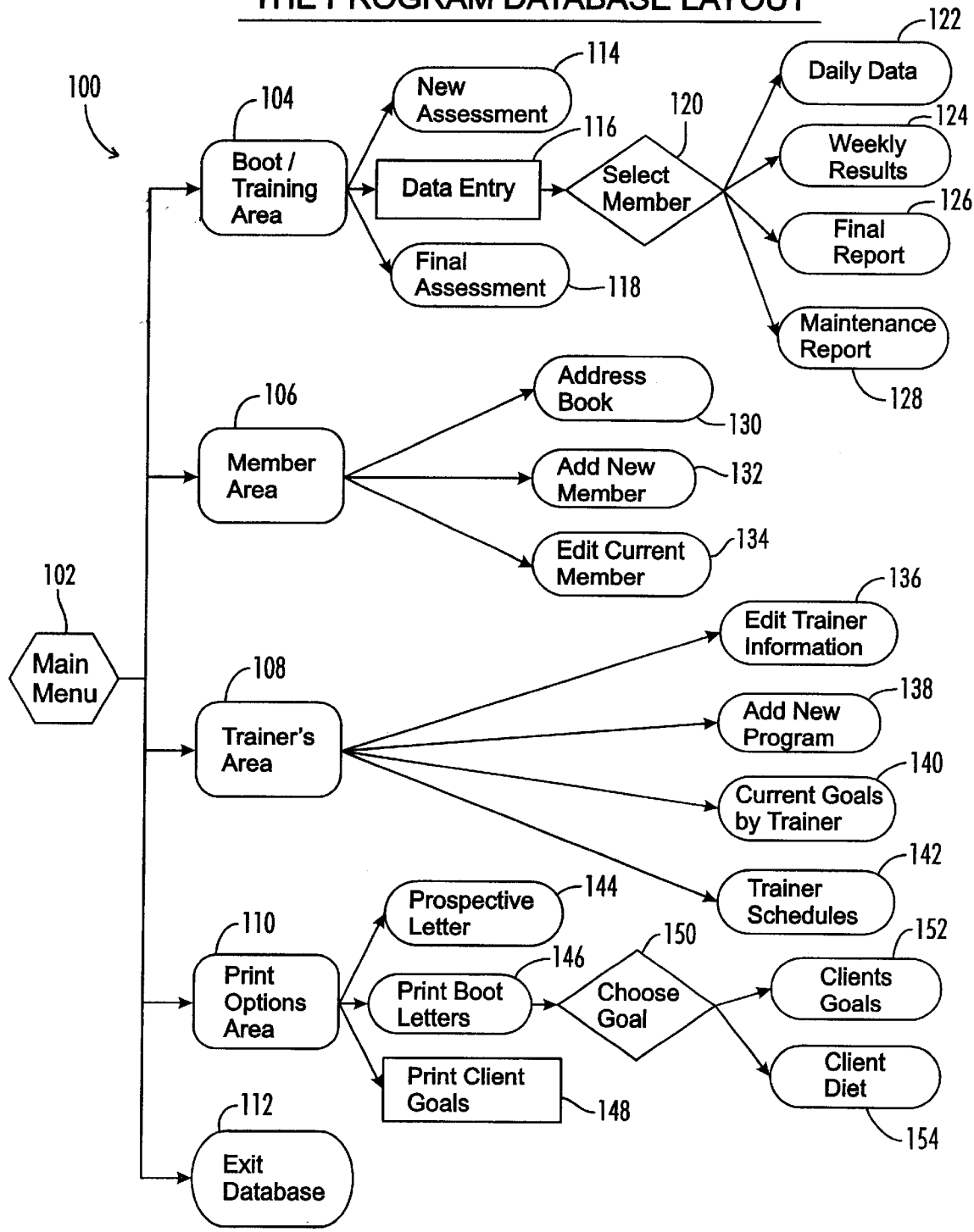
FIG. 1 of the drawings shows the fitness program database and operating system layout.

To properly understand the present system and its uses, the environment and implementation results of the system's operation should be understood. This understanding begins with five basic truths that are utilized for fitness training:

1. Long term success occurs when one develops self-reliance rather than prolonged dependence. The idea is to help people to be self-sufficient individuals that are mastering overall fitness skills.

2. The Catalyst for Motivation is Recognizable Change. Motivation changes the mind's willingness to proceed. It creates hope, optimism, and inner-strength. Efforts that produce results produce motivation. Results for this program are measured in physical improvement or change. If nothing has happened in few weeks, many people give up because slow-acting programs fail to satisfy the needs of the individual.

3. It takes at least one year to establish a new metabolic set point—the body's natural equilibrium shape and weight. The human body remembers what has already happened. This is evidenced in the scientific term 'muscle memory', as well as in the results of a practice performed by elite athletes called carbohydrate loading. The body tends to continue the systemic characteristics that the body is most in the habit of providing. But old habits die hard. After losing fat, the body will attempt to replace it for a while. The more a person allows old behavior to resurface, the more diligently the body will work to return the lost fat. A long period, such as a year, of proper fitness training can reset the body's system.

4. Lasting fat loss requires the implementation of four skills including a) Managing (not necessarily minimizing) caloric (energy) inputs; b) Hydration; c) Managing constant blood sugar levels; and d) Managing optimum protein and other nutrients.

5. Individuals who participate in the two-on-one (Buddy) system of training, have consistently produced superior results to those in one on one training. Observation suggests some of the reasons for this are the enjoyment of a partner's support, the empathy of one who shares a goal, and the spirit of positive competitive forces. Our research has indicated that buddied-up fitness program participants are three times more likely to maintain their finishing weight for one year.

The present invention provides a systematic method for using these truths and monitoring and maintaining the big fitness picture for an individual over a long period. The system does provide quick results, but no lasting change in a fitness level will occur unless something happens with the person's decision-making process internally. Similar basic process changes in business are sometimes called a new paradigm or a paradigm shift. This provides a new way to think about old issues. Specifically, this system is directed at a paradigm shift toward fitness, and its impact on a person's body shape.

The present invention and system enhances the ability to provide long term focus. Weight change, in and of itself is merely a scientific process. It can be executed through determination and conscious, yet simple, behavior modifications and repetitions. It requires no talent, but is clearly aided by behavioral skills. It is these long term skills which the present system helps to impart to anyone who participates wholeheartedly in the process.

Each individual needs to be concerned with two things. One, getting fit, and two, remaining fit. Since participants advance through stages of fitness, their leadership needs change as they develop. We have identified four phases of personal fitness development, which account for eight leadership products. The system provides a monitoring method to identify the changes in levels for the leadership products.
Leadership Products: Level 1 and Level 2 (The Basic Fitness Process).

The basic fitness process produces an average fat loss range of 12–28 pounds. This has been documented by a complete review of our efforts over the past five years by our staff and a research group. In considering what the user could expect in fat loss, use 38 years old as a median age, and use a current weight and height median of 145 and 5'4" respectively. If the user are younger and larger than the median, the user should expect losses near the 28 pound mark. If the user are older and smaller, expect losses closer to the 12 pound mark. This translates into 2.3–2.8 pounds of fat per week for the eight weeks the fitness program is generally used. The loss is greater than any other method short of fasting or surgery.
Leadership Products: Level 3 Scheduled Training Three Days Per Week The Level 3 program is created to help those who either after twelve weeks of guidance do not yet feel confident on their own in the weight room, or who are not at a required minimum level of readiness for a Basic fitness program. Our data shows that if a Basic fitness participant follows up with level 3 training, he or she is four times more likely to enjoy long term success. It is a three day a week continuum designed to promote a moderate fitness regimen, or that which is appropriate for long term maintenance of body composition.
Leadership Products: Level 4 Scheduled Training Two Days Per Week The level 4 program is the next step toward independence. This is two days per week with a coach. Level 4 participants are ready to make some decisions about how often they should be strength training (at least three times) based on their own physiology and goals. They can then use the coach for two of their workouts, and work out additional day(s) on their own.
Leadership Products: Level 5 Scheduled Training One Day Per Week Level 5 is one day per week with a coach. Again, it is important to remember that this represents only one of three or more workouts recommended. The implication here is that these individuals, enrolled in this once per week protocol, are lifting at least two additional days per week on their own. In other words, this is the final stage for those who are weening themselves to independence.
Leadership Products: Level 6, Level 7

Continuing on the road to independence, Fitness consulting affords members the opportunity to work primarily on their own, and only occasionally with leadership as needed. This is the critical stage that will give individuals the confidence they need to know how and when to adjust or change their workouts for maximum effectiveness at all times through the year.
Leadership Products: Level 6 Scheduled Consultation or Training Level 6 can be utilized for either working out with a coach, or using the time to consult on diet or cardio questions. It is recommended that members take advantage of each in level 6. That way, he or she will improve their nutrition and cardio training skills in the consultation hour, and receive technique suggestions in the training hour.
Leadership Products: Level 7—Secret Circuit This extremely high intensity program is set to private music with the coach on a wireless microphone and headset system. The individual is led all over the facility in a never stopping blast of adrenaline. This provides a maximum intensity workout in a small amount of record time.

In order to monitor the different training levels and provide an comprehensive tracking and monitoring system, the present invention utilizes a database structure and program on a computer system. The computer system is a standard desktop setup with processor, memory, screen display, inputs, outputs, printer connections and other characteristics as is well known in the art. The present system may be implemented in a program platform or language, and is shown in a Microsoft Windows™ type operating software environment.

The overall description of the present invention is described in sections as follows: Overview, Getting Started, Menus, Data Entry, Daily Data, Weekly Results, Assessments Heart Rates, Assessments Skin Folds, Assessment Goals, Assessments Metabolism, Assessments Diet Type, Assessments Diet/Cardio, Final Assessment, Address Book, New/Current Members, Member Referrals, Trainer Information, Trainer Schedules, Assessments by Trainer, Printing Goals. Each of these sections will be described in the following discussions.

Overview

FIG. 1 of the drawings shows the fitness program database and operating system layout 100. This system begins with a main menu 102 which allows access to sub-menus including the Boot/Training area 104, the member area 106, the trainer's area 108, the print options area 110, and exiting 112 the database. In the Boot/Training area 104 the user is allowed three options for either new assessment 114, data entry 116, or final assessment 118. If the user selects the data entry 116 selection then the user may select the member 120 and enter daily data 122, obtain weekly results 124, the final report 126, or a maintenance report 128. In the member area 106 the user is given selections to allow for searching the address book 130, adding a new member 132, or editing a current member 134. From the trainer's area the user is allowed the options of adding or editing the trainer information 136, adding a new fitness level program 138, providing current goals by trainer 140, or assessing the trainer's schedules 142. In the print options area 110 the user is allowed to select from a perspective letter 144, printing fitness program letters 146, or printing client goals 148. If the user selects to print client goals 148 then the user is allowed to choose the goals 150 and provide information regarding the client goals 152 or the client diet 154. Each of these areas are described in more detail in the appropriate discussions.

Getting Started

The following general information, definitions, and descriptions provide information regarding the use of the software as detailed in this description.

Basic definitions of terms Used in the Instruction Manual include:

Button—Small squares (generally shown in gray with pictures on them) that are utilized to activate a command when clicked with the mouse button.

Form—A form is what appears on the screen for data entry or for selecting different options.

Field—A field is a blank where information is entered. There are two different types of fields. The first is simply a box where the user type in data. A second type of field is called a "List Box" because it contains a list of data from which to choose. This field has an arrow on the right side of the box. Clicking on this arrow displays a list, along with a scroll bar to move through the list.

Report—A report typically looks like a letter or other document that is printed out. In this program, Goals and Assessments, Diets and New Finishes are all reports.

Tabs—The assessment form contains a series of Tabs that lead the user through different steps of the assessment process. They look similar to what is used in standard spreadsheet or accounting programs. The user may click on the top of the tab to select each sheet.

Entering Data—General Guidelines for entering data includes moving from field to field, entering dates, entering percentages, working with list boxes, and saving data.

1) Moving from field to field. There are a few different ways to move from field to field in this program: a) Hit the Tab key, b) Hit one of the arrow keys on keyboard and c) use the mouse to point on the field and click once. This program has not been designed to use the ENTER key to move to the next field.

2) Entering Dates. The user can choose any typically recognized form of entering dates and can choose from any of the following formats: 01/01/00; 1/1/00; 1/1/2000.

3) Entering Percentages. There are a few areas where the user is asked to type in percentages. Rather than typing in "100" for 100%, the user should type the number as a decimal. Ie: For 100% type 1.0, For 80% type 0.8.

4) Working with List Boxes. To display the list, the user should click on the arrow with the mouse. The user can then use the scroll bar to move up or down the list. Once the user finds the selection on the list, they may click once to highlight it and hit the TAB key to select it. Any time the user has a list, the user can always start typing in the characters of the name the user is looking for rather than clicking on the arrow. As the user types, the matching selection will appear. The user may then hit the TAB key to select the matching selection from the list.

5) Saving Data. Every time the user exit a field, the information is automatically saved. The user does not have to press any button to save the data.

Menus

FIGS. 2 through 6 show the main accessing menus for the fitness program structure.

Figure 2:
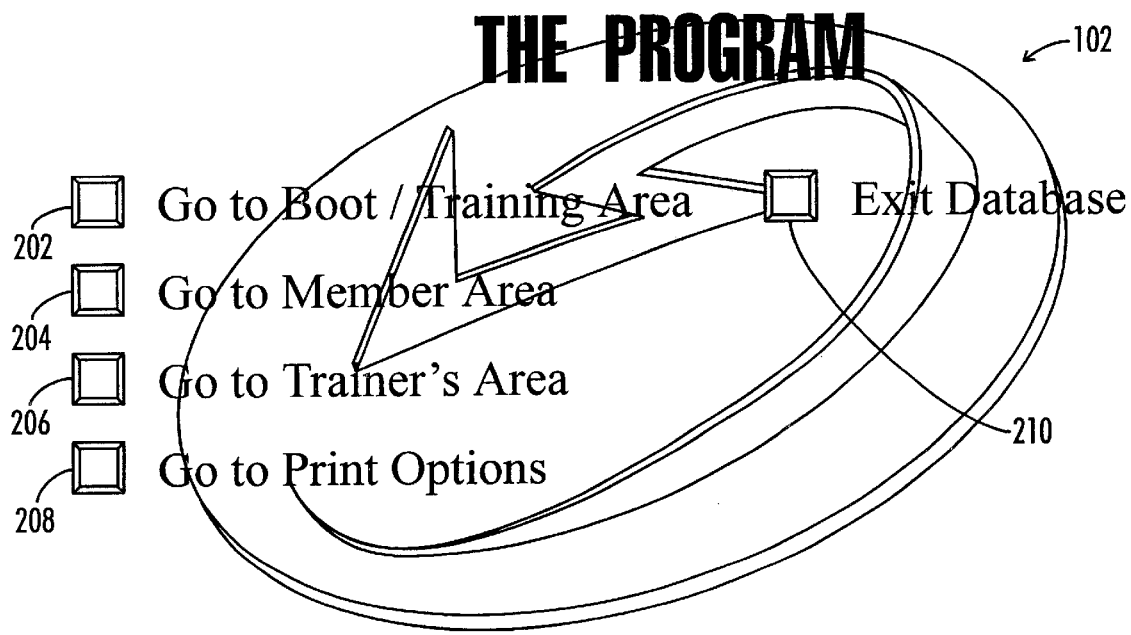
FIG. 2 shows the main menu.
Figure 3:
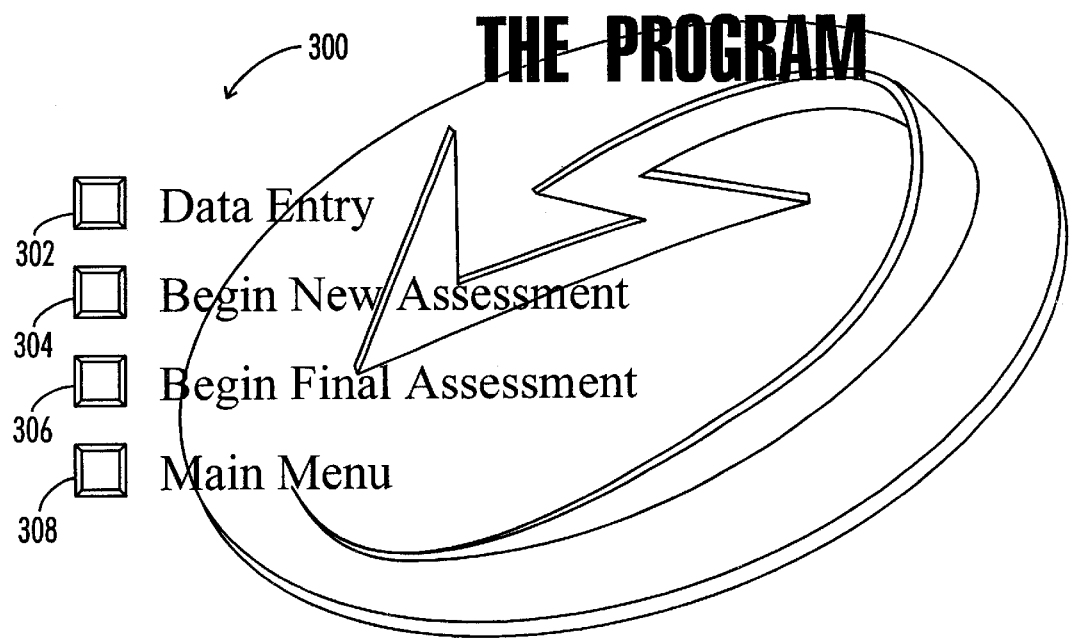
FIG. 3 shows the initial fitness program/training sub-menu.

FIG. 2 shows the Main Menu 102. Every time the user open the fitness program database, the Main Menu 102 will open. The main menu 102 consists of five option buttons 202, 204, 206, 208, 210 leading the user to different areas of the database. Point the mouse to the button and click once to activate the option the user select. The options are:

Go to initial fitness program/Training Area 202—Takes the user to the Boot/Training Sub-Menu 300 shown in FIG. 3.

Figure 4:
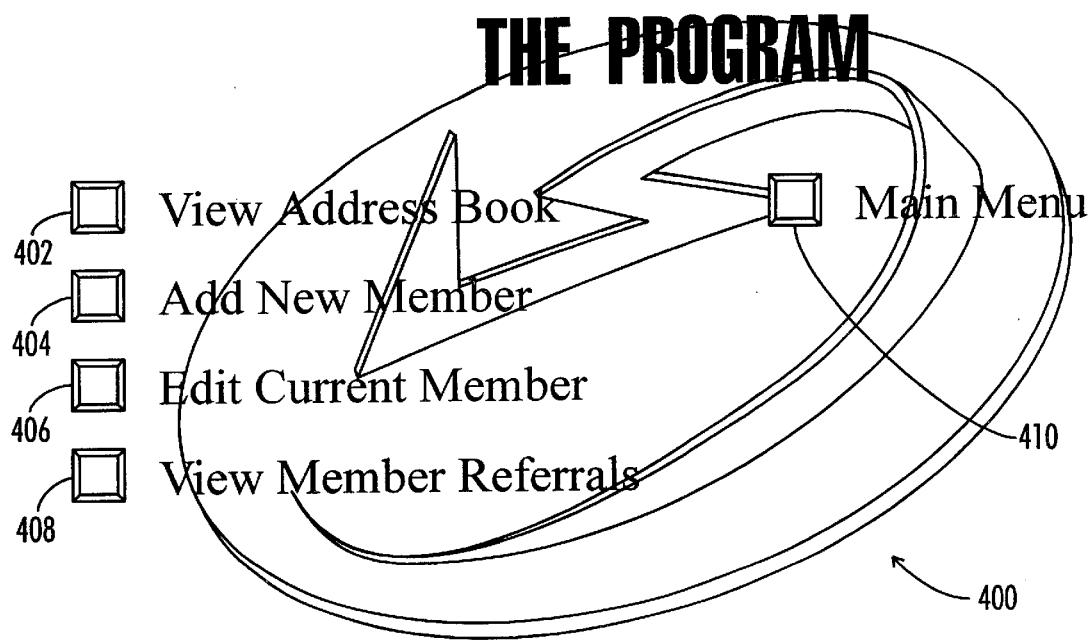
FIG. 4 shows the member sub-menu.

Go to Member Area 204—Takes the user to the Member Sub-Menu 400 shown in FIG. 4.

Figure 5:
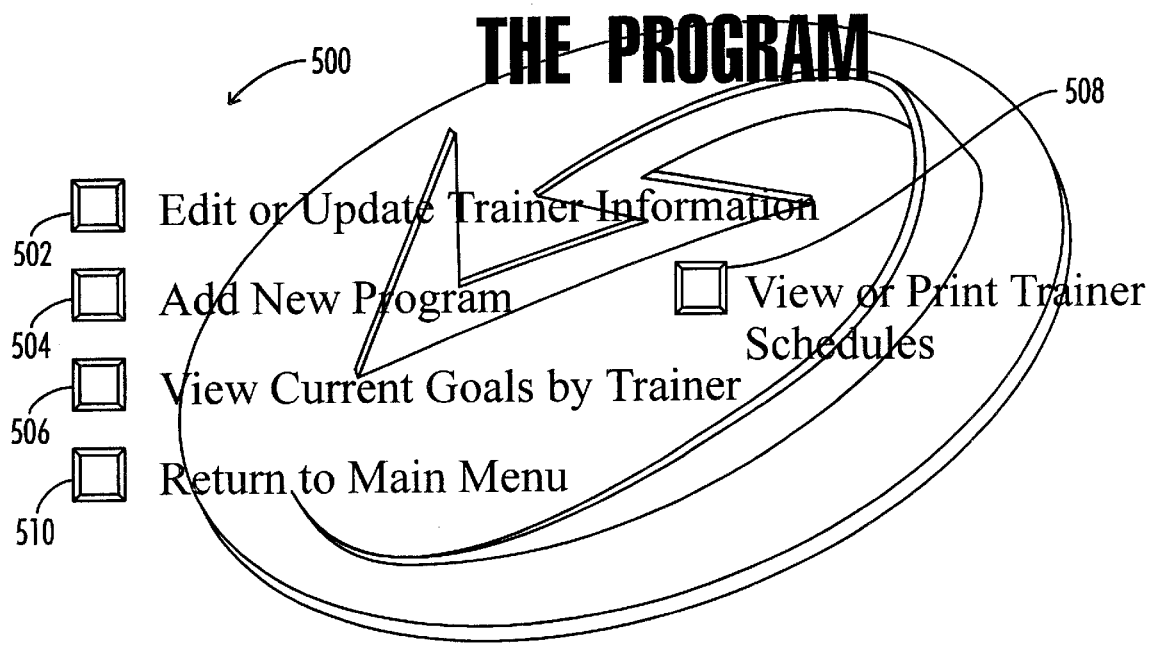
FIG. 5 shows the trainer's sub-menu.

Go to Trainer's Area 206—Takes the user to the Trainer's Sub-Menu 500 shown in FIG. 5.

Figure 6:
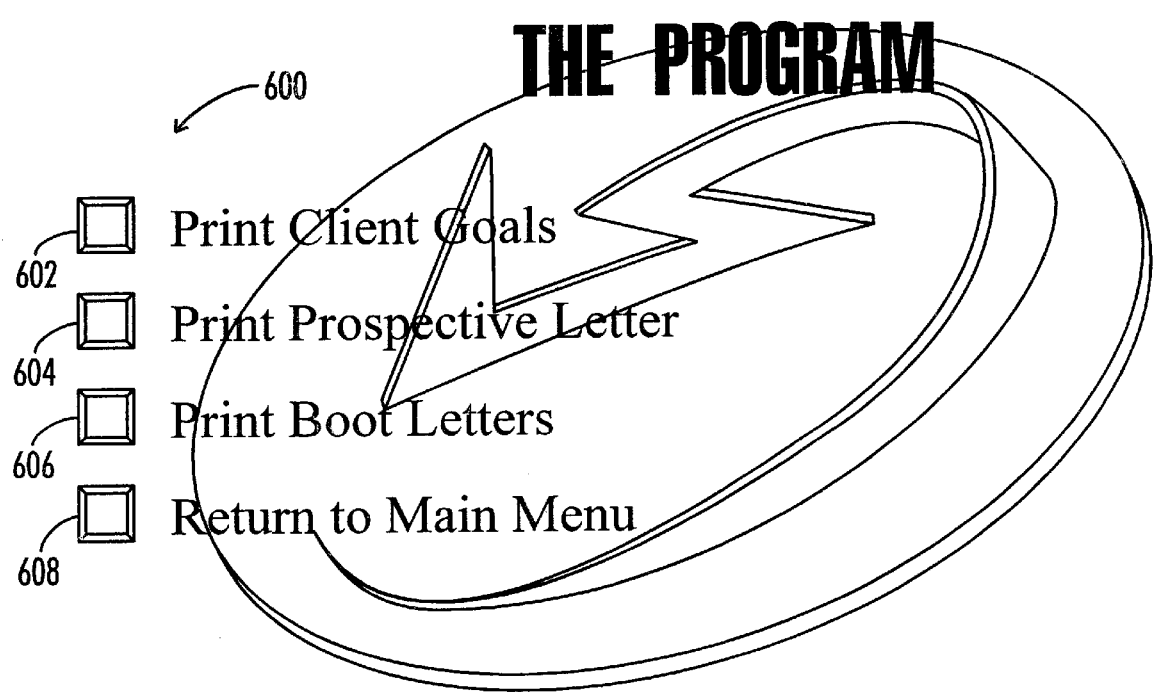
FIG. 6 shows the print options sub-menu.
Figure 9:
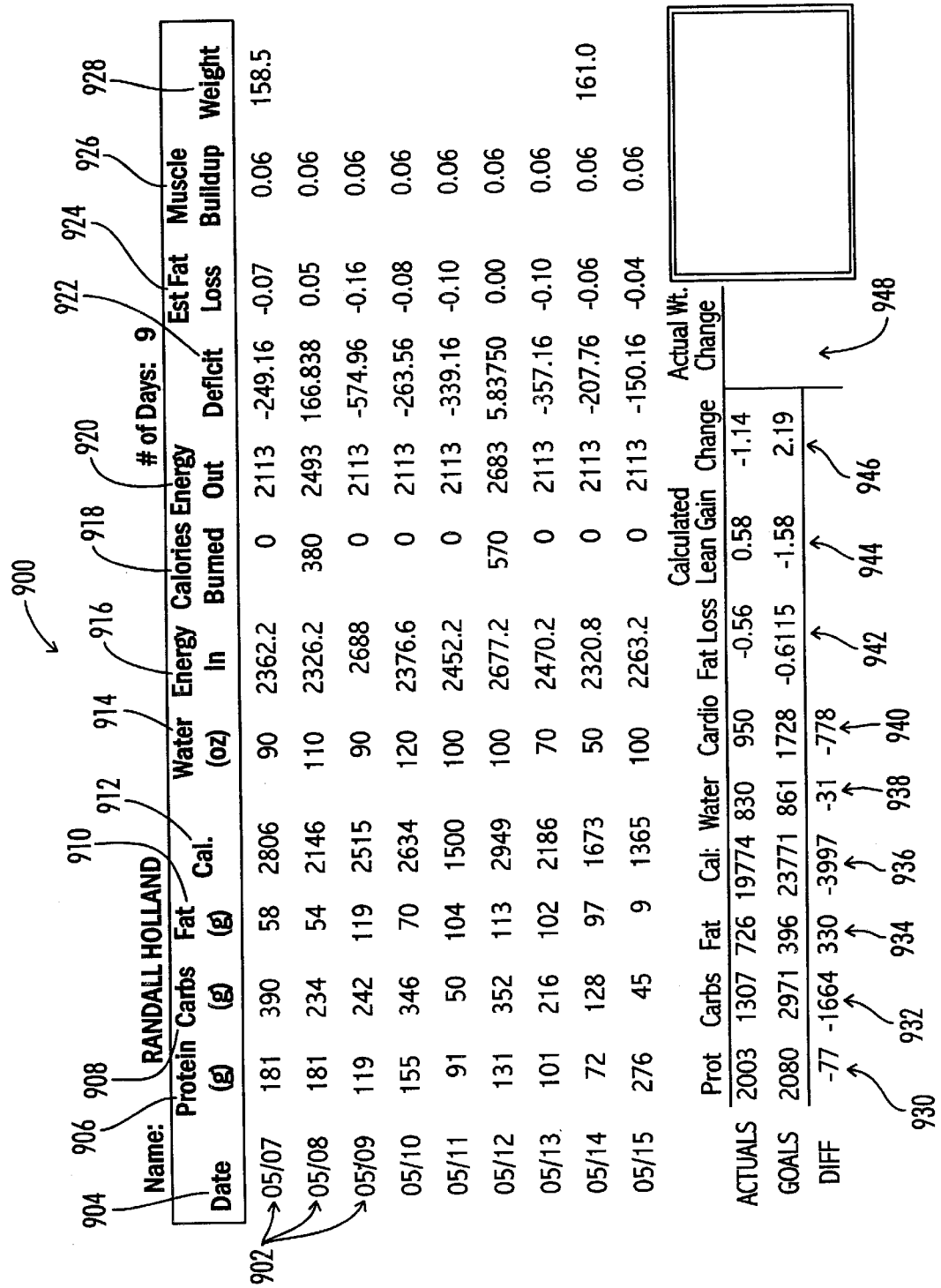
FIG. 9 shows the weekly results form.

Go to Print Options 208—Takes the user to the Print Options Sub-Menu 600 shown in FIG. 6.

Exit Database 210—Exits the fitness program database. For the present embodiment, the user can move between Sub-Menus 300, 400, 500, 600 and the Main Menu 102 by selecting the button with the name of the menu choice. The user cannot move from one Sub-Menu directly to another Sub-Menu. The user will always have to move through the Main Menu 102 to get to another Sub-Menu. Also for the preferred embodiment, the Main Menu 102 is the only menu that allows the user to Exit 210 the fitness program database. Other programming methods may be utilized for different access options if desired but this method was chosen for the preferred embodiment.

Boot/Training Sub-Menu 300

The initial fitness program/Training Sub-Menu 300 shown in FIG. 3 allows the user to enter different initial fitness program/Training forms. From this menu the user can enter new data 302, begin new assessments 304, begin "final" assessments 306, or return 308 to the Main Menu 102. The user's selections are as follows:

Enter New Data 302. This takes the user to a form described in FIG. 7 that allows the user to enter new data on a specific member. From this form, the user is able to access the following areas of the database: Enter Daily Diet and Cardio data for initial fitness program clients; View/Print Member Weekly Results; View/Print Difference between two Assessment Dates; and View/Print Final Maintenance Guide for initial fitness program Clients.

Begin New Assessment 304. This takes the user to a form shown in FIG. 10 that allows the user to enter a full assessment on any client in the database. The user will use this option for any New Initial Fitness Program Assessment, any Mid-Assessment, or any New Assessment that requires diet and cardio goals.

Begin Final Assessment 306. This takes the user to a form similar to the form of FIG. 11 to enter a final assessment on any initial fitness program client or other members in the database. This form does not include sections for cardio and diet goals but is used only for entering final tape measurements and skin fold information to compare with a previous "new" assessment.

Member Sub-Menu 400.

The Member Sub-Menu 400 allows the user to choose from four different member areas 402, 404, 406, 408, or to return 410 to the Main Menu 102. The user will point the mouse to the area the user want to go to and click once on the button. The user's choices are as follows:

View Address Book 402. This takes the user to a form shown in FIG. 19 that displays all members currently in the fitness program database. This screen will display member names, addresses and phone numbers. The Address Book allows the user to search for members by last name. No Data Entry is allowed in this screen.

Add New Member 404. This takes the user to a form shown in FIG. 20 to enter information on a member that does not currently exist in the system. On this screen, the user can enter current members (or prospective members), assign them a Member ID Number and add address and phone information. The user can also register the member to a specific trainer and training program on this screen.

Edit Current Member 406. This takes the user to a form similar to that shown in FIG. 20 to update information on a current member. The user can easily search for a specific member to update. Most often, this form will be used to update or change the training program of the member. It is important to keep this information updated as members switch trainers or programs.

View Member Referrals 408. This takes the user to a form shown in FIG. 21 that displays any members who have referred current members or prospective members. This form should help track any bonuses or awards given to current members for referrals.

Trainers Sub-Menu 500

The Trainers Sub-Menu 500 allows the user to enter different Trainer options 502, 504, 506, 508 or return 510 to the Main Menu 102. The user's selections are as follows:

Edit or Update Trainer Information 502. This takes the user to a series of individual forms stating at the form shown in FIG. 22 for each trainer. New trainers can be added, and current information and pictures can be added or updated. This form includes education, training experience, specialty and address and phone information.

Add New Program 504. Clicking on this option will pop up a list of current programs. This allows the user to enter new training programs to the database. New training programs must be added prior to the beginning of each initial fitness program session or any time new items are added to the fitness program.

View Current Goals by Trainer 506. This takes the user to a form displaying all of the members working out with different trainers along with their current goals. This form can be used to compare the different goals set by individual trainers.

View or Print Trainer Schedules 508. This takes the user to a form shown in FIG. 23 that displays all of the members working out with each trainer, by training time. It also includes the member's phone numbers, so it is a good place to go to for a quick reference for cancellations or re-scheduling.

Print Options Sub-Menu 600

The Print Options Sub-Menu 600 allows the user to go to commonly printed reports without going through other areas of the database, and allows the user to return 608 to the Main Menu 102. The user's choices are as follows:

Print Client Goals 602. This takes the user to a form shown in FIG. 25 where the user can print specific client goals. The user selects the member from the list given and the user will be able to print the initial fitness program Goals or the initial fitness program Diet goals.

Print Prospective Letter 604. This will take the user to a pre-written letter welcoming prospective members to joint the fitness program. It will automatically generate and print the letter to all members currently listed as "Prospective" in the database.

Print initial fitness program Letters 606. This takes the user to a form shown in FIG. 26 that allows the user to generate letters to initial fitness program clients or other members of different training programs. The standard initial fitness program Welcome Letter and initial fitness program Meeting Letters can be automatically generated using this form.

Data Entry

The Enter New Data form (Boot/Training Area) 700 will be the most commonly used form for trainers with initial fitness program clients. This form can be used to enter Daily Diet and Cardio information 708, view Weekly Results 710, view end of boot results 712, print Maintenance Guides 714 for initial fitness program Clients, or view Differences 720 between Assessment dates 716, 718. The following steps may be utilized for using this Form.

Please Select Trainer 702. The user will click on an arrow to the right side of the box following these words. A list will appear of all of the trainers. The user can use the scroll bar to move down the lists of trainers. Once the user finds the name the user is looking for, the user will click on the name to select it. The user may then hit the TAB key to select the trainer and move to the next part of the form.

Please Select Workout Time 704. The user will click on an arrow to the right of the box following these words. A list will appear of different workout times, ranging from opening to close such as 6:00 AM to 8:00 PM. The user can use the scroll bar to move down the list of times. The user will then click once on the time the user would like to select and hit the Tab key to select the time and move to the next part of the form.

Choose Member 706. The user will click on an arrow to the right of the box following these words. A list of members associated with the Trainer and Workout Time the user selected will appear. If the user does not see the member the user is looking for, the user may try one of the following. Click once on the button "Select New Member" 722 on the bottom left of the screen and then select trainer and training time again (following procedure above). The user should make sure that the user has assigned the member the specified Trainer and Training Time. Alternatively, the user may close this form, go to the Main Menu 102, go to the Members Area 204, go to Edit/Update Current Member form and follow the instructions for this form.

The user may also click on one of the following buttons to view or add information.

Figure 8:
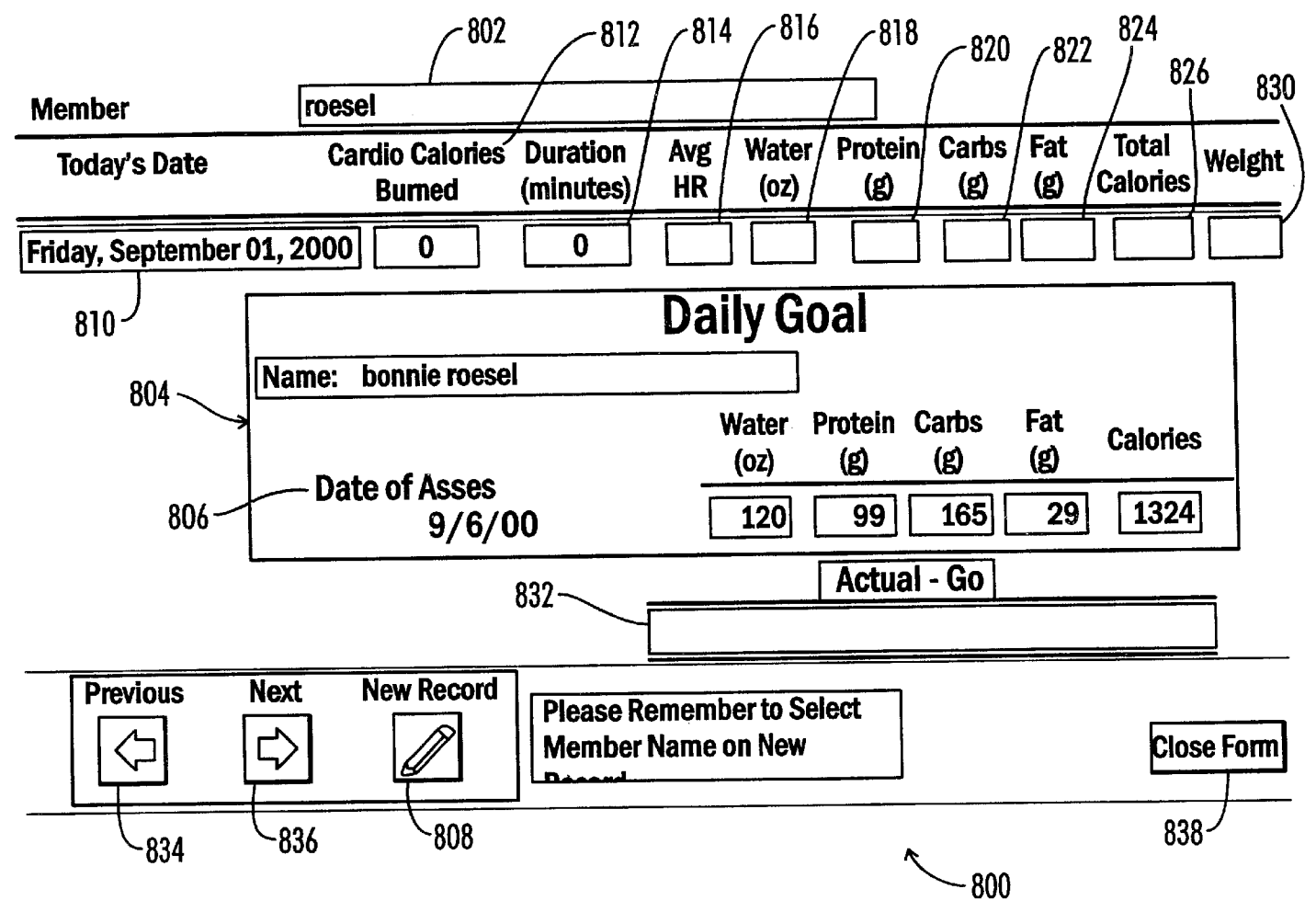

Enter Daily Data 708. This button is used for Entering Cardio and Diet Data as shown in FIG. 8. This button will take the user to the last entry that was made for this member. The user may then Click on "New Record" to add new information. The blank form will default to the day immediately preceding the current date (Yesterday's date) to allow for the collection of all data for one day with entry on the next day. To enter data for a different date, the user simply changes the date.

View Weekly Results 710. When the user clicks this button, the user will be asked to enter a Beginning and Ending date for comparing data. The user will enter data in the format "5/11" or "05/11" then either hit the Return key or click the mouse on OK after each date. Typically, weights are measured on a consistent week day such as a Mondays. To compare actual weight changes with predictions, the user would choose the dates of the different Monday's. This will actually compare 8 days, but all calculations (including goals) take into account the ACTUAL number of days selected. If the user wants to view more or less than one week's worth of data, the user is able to do so by selecting the dates of the user's choice.

A view Assessment Differences button may also be provided (not shown). This will automatically show the client's difference between their most recent "Initial Assessment" and most recent "Final Assessment".

Print Final Results Report (End of Boot Results) 712. This will print a report based on the client's most recent "Initial Assessment" and most recent "Final Assessment." This report includes the weight loss, body fat change and total inch change of the client during the initial fitness program process.

Print Maintenance Guide 714. This will print a guide the member can use during their maintenance phase, based on their actual achievements during the initial program. It includes the average food intake of the client, their "equilibrium" metabolilsm and diet and cardio guides.

The user may also compare changes in specific assessment dates. There are times when the user may want to compare date other than the start date and end date of the initial fitness program process. For example, comparing the mid-assessment with the final assessment, or perhaps last year's results with current results. This option allows the user to specifically select the dates the user wants to compare.

For First Date 716, the user will click on an arrow to the right of the box following these words. All of the assessment dates for the client will be listed. Caution, if initial assessment dates are grouped and final assessment dates are grouped, this list will not necessarily in order by date. The user may then click once on the date the user would like to select and hit the TAB key to move to next date.

For the Second Date 718, the user will follow the same procedure as with the First Date and choose the second date the user would like to use for comparison.

The user may then click on the "View Change" button 720. After the user has chosen the two dates the user would like to compare, they will then click on the "view Changes" button to view the differences. This will generate the same report as the "View Assessment Changes" button, but with the dates 716, 718 the user specifically have selected rather than the initial fitness program assessment dates.

For the Select New Member 722, this button clears the current form to allow the user to select a different Trainer, Training Time and Member. This option allows the user to scroll through different members without having to move to a different area of the database. After the form is cleared, the user follow any of the above procedures to enter the data of the user's choice.

The user may also close this page with the close button 724.

Daily Data

The Enter Daily Data button 708 takes the user to a daily data form 800 for entering daily diet and cardio information. Since the user has already selected the member, the member's information 802 will appear when the form opens. The most recent goals 804 established for the client, along with the assessment date 806, will also appear on the form 800. The user may use this form for Entering Data.

When the user open this form 800, it will go to the most recent record entered for the member. If no records have been entered for this member, it will open to a blank form showing Yesterday's date which can be changed as appropriate. To enter new data, the user will click on Enter New Record 808 and follow the instructions. As soon as the user begin a new record by selecting the new record button 808, the user must select member name 802 from a list. The user will do this for every new record the user enter for every member. Yesterday's date 810 will automatically appear. To change the date, the user will simply enter the field, hit the delete key and type in the date 810 the user wishes to enter and hit the Tab key to move to next field. Next the user will enter the cardio calories burned 812. The default for this field is "0", so if the client did no cardio, then the user will hit the Tab key to move to the next field. If the member does cardio later in the day, the user will be able to access this record again to make updates. For Duration 814 (minutes), the user will type in the minutes the client spent doing cardio and then hit the Tab key to move to the next field. For Average heart rate 816, the user will type in the average hear rate of the client during cardio and hit the Tab key to move to the next field. For Water 818 (oz), the user will type in the total ounces of water the client drank that day, hit the Tab key to move to the next field. For Protein (g) 820, the user will type in the total protein grams for the day, based on the client's diet and move to the next field. For Carbs (g) 822, the user will Type in the total carbohydrate grams for the day, based on the client's diet and move to the next field. For Fat (g) 824, the user will type in the total fat grams for the day, based on the client's diet and move to the next field. Total calories 826 will be automatically calculated based on Protein, Carbohydrate and Fat intake. The user cannot make any changes to the "Total Calories" field. If the calories are off, the user can go back and adjust the total grams of protein, carbohydrate or fat. To move to the previous fields, the user can use the left-arrow key on the keyboard, or hit the Shift key and Tab key together. The Weight field 830 is for entering the client's weight when it is measured. This field 830 will be left blank on days that weight measurements are not made.

"Daily Goals"

As previously noted, the client's daily goals 804 appear on the form, as well as the actual goal difference 832 between the client's daily entry and their goal. This information cannot be changed or edited, but should be used to assess how well the client is maintaining his or her goals.

For Changing Previous Records, the user can access records entered on previous days by using the arrow buttons 834, 836 on the bottom left of the form 800. The user may click the previous arrow to move back one record. Multiple days may be moved by clicking the previous arrow 834 as many times as necessary to find the record the user need. When the user gets to the first record, the computer will indicate the user cannot go backwards any further. The user may then edit, update or change any information the user desires. Click the right or next arrow 836 will move the user forward one record. When the user get to the last record, the computer will indicate the user cannot move forward any further. The user may then edit, update or change any information the user desires.

The user may click the New record button 808 if the user wants to create a new record. The user will choose the new member name for each new record and enter the correct the date of the new record. The preferred embodiment is limited so that only one record per day per client is allowed to avoid multiple entry of information.

Finally, the user may also select to exit the form when the user is finished with entering the information on this form by clicking once on the button marked close form 838. This will return the user to the "Data Entry" form 700.

Weekly Results

The Weekly Results form 900 allows the user to view a client's changes over a week or any other time period. The user accesses this page from the Initial fitness/Training Sub-Menu 300 by clicking on Data Entry 302 and selecting the member's name as shown in FIG. 7. The user will then click once on Weekly Results 710 to view the weekly results form 900. When the user click on the weekly results button, the user will be asked to enter a beginning and ending date for comparing data. The user will enter data in the format "5/11" or "05/11" then either hit the Return key or click the mouse on "OK" after each date. To compare actual weight changes with predictions, the user will choose the date of the two different weight measurement days. If two Mondays are selected, this will actually compare 8 days, but all calculations (including goals) take into account the actual number of days selected. If the user wants to view more or less than one week's worth of data, the user is able to do so by selecting the date of the user's choice. The data is displayed for the user. A record 902 will be displayed for the dates selected. If all of the records do not fit in the screen, the user will see a scroll bar on the right side of the screen which the user can use to move between the dates. Each day will show the following information: Date 904, Actual caloric intake 912 including protein 906, carbs 908 and fat 910 (entered as shown in FIG. 8 as 826, 820, 822, 824), Actual water intake 914 (entered as 818), Energy in 916, Total cardio calories burned 918(entered as 812), energy out 920, Calculated caloric deficit 922, Estimated fat loss 924, Estimated muscle build-up 926, and weight 928 (entered as 830). The bottom displays a summary showing: Total caloric intake versus goal 930, 932, 934, 936, Total cardio versus goal 940, Total water intake versus goal 938, Total calculated fat loss & lean gain based on actual numbers and goals 942, 944, 946. The Actual weight change 948 shows only the actual difference between the two weight measurements within the dates chosen. If more than two weight-ins are included in the data selected, this will measure the largest weight difference.

ASSESSMENTS

The Assessments forms shown in FIGS. 10 through 18 may be accesses from the Initial fitness/Training Sub-Menu 300 by clicking on Begin new assessment 304 or begin final assessment 306. Tabs will then be presented to access each of the assessments forms as described herein.

Assessments Heart Rates

The New Assessment option and associated heart rate form 1000 shown in FIG. 10 is for entering member assessment data at the beginning of a Initial fitness session, or any time a member is being assessed to set net goals. The "final assessment" form is used at the end of a Initial fitness session, or to compare any client's results with previously set goals, where no new goals are set. This form may be accessed by clicking on the tab with the same name. Once accessed, the user may move through the fields for the assessment.

For member 1002, the user will click on the arrow to the right of the field to display a list of members. The list contains all current members in the database. To help with the user's search, the user may begin typing in the member's last name. When the user has located the correct name, they may then click on the name with the mouse to highlight it, then hit the Tab key to select.

For date 1004, today's date will automatically appear. If this is correct, hit the Tab key to move to the next field. To change the date, hit the Delete key, type in new date and hit the Tab key to move to the next field.

For Age 1006, the user will enter in the member's age. This is important because it is used to calculate the member's heart range targets. The date of birth could also be collected and stored to calculate this number automatically. However, many people may consider this to be personal information. Thus the present system does not store this information. Once the age is entered, the user may then hit the Tab key to move to the next field.

For Sex 1008, this field has a list containing "male" or "female". The user will click on the arrow to display the list and click on the correct selection or type in the letter "m" for male or "f" for female to make the user's decision. Once finished, the user will hit the Tab key to move to the next field.

For Assessor 1010, this field will list all of the current trainers. The user may click on an arrow to display the list, and then click on the correct name to highlight it and hit the Tab key to make the user's selection. Trainers are listed in alphabetical order by last name.

The user will also select whether this is an initial assessment 1012. This is a very important selection to properly record the information for later use as described in this specification. The user will check the initial fitness program box 1014 to set this current assessment as the goals used to calculate the client's progress throughout the program. The user should check this box for any beginning of Initial fitness assessment. The user will check a separate box 1016 if this is a mid-term assessment, or if the user does not want to use the goals to calculate the client's progress. Note: At least one assessment must be selected as an "Initial" for every member.

For Heart Rates 1018, the default resting heart rate is 62. The user will type over this amount if the user knows the client's actual heart rate and it the Tab key to move to the next field.

For target heart rate ranges 1020, 1022, 1024, the default settings are lower 70%, middle 78%, and top 82%. If these are incorrect, the user can type over the percentages and set the user's own. The actual heart rates will be automatically calculated based on the percentages selected and the member's age. When the user has completed this page, they will then click on the tab marked skin folds to move to the next section.

Assessments Skin Folds

FIG. 11 shows the skin folds measurements section screen 1100. To access this section, the user will point the mouse and click on the tab with this name. This screen is used to acquire information from a 7-Site Jackson, Pollock and Ward examination. The user will type in the measurement for each of the sites listed for chest 1102, axilla 1104, triceps 1106, subscapula 1108, abdome 1110, suprailium 1112, and thigh 1114. The user will hit the Tab key after each entry to move to the next field. The total 1116 is automatically calculated. There is no maximum or minimum allowed, so the user will type in all actual numbers as they are measured. After entering thigh 1114, the user will hit the Tab key to move to the tape measurement section for entering tape measurements. The user will type in the measurement for each site listed including shoulders 1118, chest 1120, waist 1122, hips 1124, upper arm right 1126, upper arm left 1128, thigh right 1130, and thigh left 1132. The user will enter numbers in decimals rather than fractions and hit the Tab key after each measurement. The user will then click on the calculate button 1134 to use these items. When the user has completed this page, they will then click on the tab marked goals to move to the next section.

Assessment Goals

To access this section, the user will point the mouse and click on the tab with this name. Based on the skin folds measurements taken in the form shown in FIG. 11, the client's weight 1202, body fat % 1204, lean weight 1206 and fat/fluid weight 1208 will appear in the goals page 1200 shown in FIG. 12. If these do not appear, make sure the user has entered the member's weight and that the user has pressed the calculate 1134 button on the previous page.

Figure 13:
FIG. 13 shows the water guideline window.

The user will then enter the Predicted fluid loss 1210. This is often difficult to predict. For help, the user may click on the "water weight" button 1212. A water guideline window 1300 will appear as shown in FIG. 13 with a list of body fat % 1302 along with typical water weights for men 1304 and women 1306. The user can use a scroll bar to move down the list to find the member's actual body fat %. The user may click on the close button 1308 when the user is finished to return to the goals page 1200. The user will then enter in the recommended water weight loss 1210 from the chart 1300. If the member has a high-sodium diet, or if they are not currently drinking a lot of water, the user will adjust this amount by ½ lb. of water for each. The user will then hit the Tab key to move to the next field.

For Goal 1214, the user will discuss and obtain the client's goal, type in the goal weight 1214 and goal lean weight 1216 and hit the Tab key to move to the next field. The body fat % 1215 and fat/fluid weight 1217 will automatically be calculated. The user can adjust the goal weight 1215 and goal lean weight 1217 until the user comes up with an overall goal the user and the user's client are satisfied with. The user will then enter the total weeks 1218 of the program. The default setting is 8. This number will calculate 1220 the average weekly changes the client must hit to meet their goals. The user will then look over these weekly numbers carefully to make sure the goal is realistic. When the user has completed this page, they will then click on the tab marked metabolism to move to the next section.

Assessments Metabolism

The predicted metabolism screen 1400 shown in FIG. 14 may be accessed by clicking on the tab with this name. The click for metabolism worksheet 1402 is used to display the predicted metabolism worksheet 1500 shown in FIG. 15. No data can be entered into the worksheet 1500, but it can be printed out for the client to use. The information on this form explains the calculations for acquiring the energy levels throughout the day. The user may close this form when the user is finished viewing the information by clicking on the close button 1502 and the user will be returned to the predicted metabolism screen 1400. For the sum of predicted metabolism 1404 the user will type in the total number of 1's 1406, then hit the Tab key to move to the next field and repeat this process for numbers 2 through 6 1408, 1410, 1412, 1414, 1416. The total 1418 will be automatically calculated. Because of the "0" for cardio time, the total number should be 23 in accordance with the remaining hours in the day. If the user's total does not sum up to 23, the user will make the necessary adjustments. The user will then click on calculate 1420 to calculate the member's daily metabolism 1422. When the user has completed this page, they will click on the tab marked diet type to move to the next section.

Assessments Diet Type

The CAMS/PAMS screen 1600 is shown in FIG. 16 and used for calculating carbohydrate utilization and protein utilization. To access this section, point the mouse and click on the tab with this name. This page 1600 has a series of questions that will help to evaluate the amount of carbohydrate calories that will be utilized towards creating muscle mass. Question #4 will take into consideration any recent diets that may have adversely affected the member's metabolism. The user will help the member to answer the following questions. 1) I have had problems with my weight 1602. Answers for this question are My whole life, Most of my life, In recent year, or Never. 2) I weight train strenuously on a regular basis 1604. Answers for this question include 0 Days/Weeks, 1–2 Days/Week, or 3+Days/Weeks. 3) When I try I am (fill in the blank) in losing weight 1606. The answers are Unsuccessful, Somewhat successful, Successful, or Very successful in losing weight. 4) Check if the user have been on a high protein/or carbohydrate depletion diet 1608. If this is selected then the user will be asked about the # of months on diet 1610, the # of pounds lost 1612, the # of months since diet 1614, and the # of pounds gained since diet 1616.

After completing the questions, the user will click on the button to calculate CAMS 1618 to determine the proportion 1620 of carbohydrate calories to protein calories that will be utilized for muscle build up.

CAMS 1618 is the Carbohydrate Allotment for Muscle Synthesis. Actual muscle mass is increased by increasing the size of individual muscle fibers. Muscle fibers are enlarged through the accumulation of carbohydrate and water into the muscle. Carbohydrate needs to be thought of as two separate substrates: specifically, fuel for expenditure, and bulk for lean mass. Every individual has a unique ability (Genetically determined) to add muscle mass. Individuals who have a high propensity to acquire mass will synthesize a greater amount of ingested carbohydrate into lean tissue. Alternatively, individuals who have a low propensity to acquire mass will synthesize a smaller amount of ingested carbohydrate into lean tissue. It is necessary to change the amount of predicted carbohydrate being expunged for fuel usage, adding the correct amount to the predicted muscle mass increase. The CAMS calculation predicts this uptake. The questions answered by the client determine the percentage of this allotment. The range is up to but not greater than ten percent (10%) of total carbohydrate calories.

When the user has completed this page, they will click on the tab marked diet type to move to the next section.

Assessments Diet/Cardio

FIG. 17 shows the Diet and Cardio screen 1700. To access this section, the user will point the mouse and click on the tab with this name. For Daily Diet 1702, the user will select the appropriate diet for the client. The user may click on the suggest diet button 1704 to determine what diet the computer has calculated in accordance with the member's body fat %. The user may then Choose diet 1706 by selecting one of two diets from the list including a 30% protein or 35% protein diet. The user can select either the one suggested by the computer or the other diet.

For PAMS and CAMS 1708, the user will enter the PAMS number 1710. PAMS 1710 is the Protein Allotment for Muscle Synthesis. While muscle mass is increased by increasing the size of individual muscle fibers, proper protein can and will limit the total muscle acquired. Ultimately, only a small amount of protein is utilized in mass augmentation. The default value is ten percent (10%) of total protein calories for PAMS 1710. The number for CAMS 1712 is automatically calculated based on questions answered previously and cannot be changed. The user is allowed to select numbers between 5% and 15% for protein utilization. (Type in "0.05" for 5% and "0.1" for 10%). If the user types in number larger than 15%, the computer will give the user an error and re-set the numbers to 10%. If the user needs to enter numbers larger than 15%, the user can do this by clicking on the help button and entering in the correct password. If the user type in the incorrect password, the user will be forced to choose a number between 5% and 15%.

For percent daily metabolism 1714, the user will enter the percent of the member's total daily metabolism that the user wants the client to eat on a daily basis. Typically, this will be between 90% to 100%. The user can enter percentages greater than 100%, but the computer will ask the user to confirm the number. The total daily calories 1716 will be calculated using the metabolism number. The user may then press Calculate 1718 for the client's diet 1720, cardio goals 1724 and water intake goals 1722. The user may also click once on the comments button 1726 to move to the next section.

Figure 18:
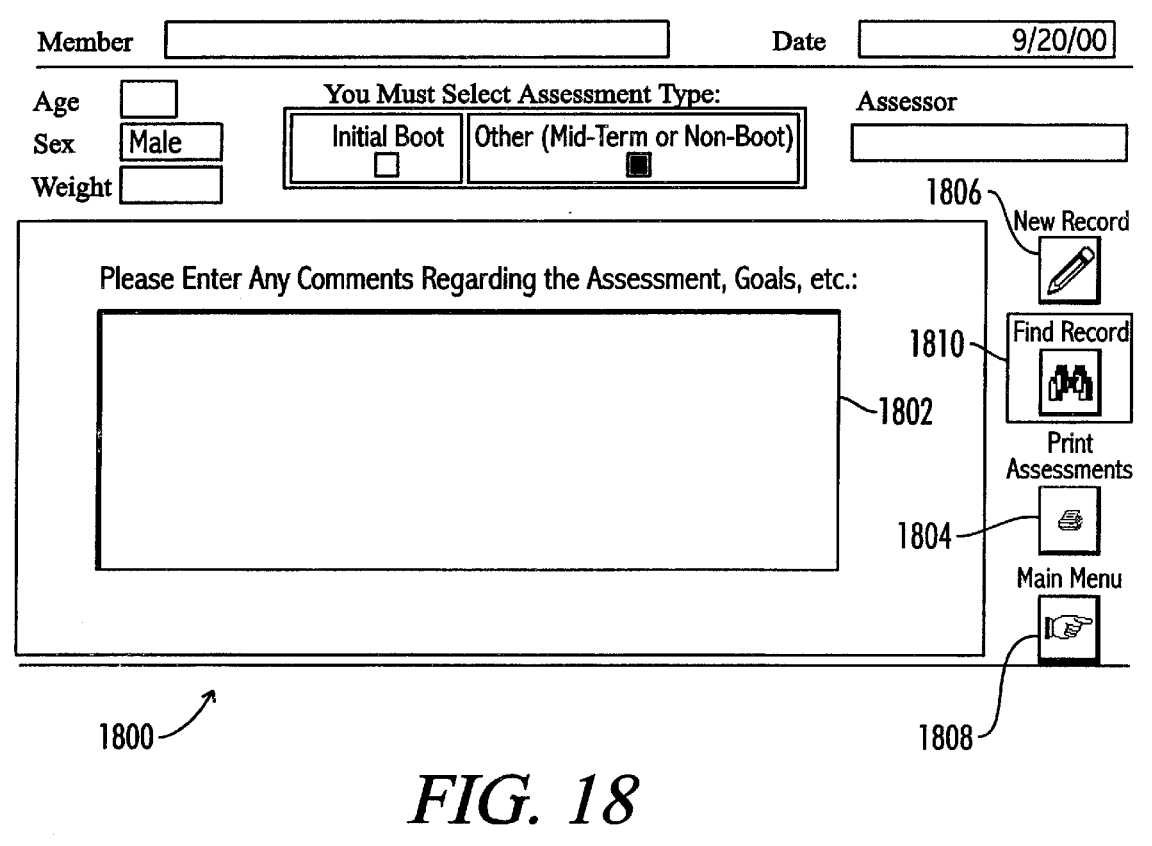

For the Comments page 1800 shown in FIG. 18, the user may access this section by pointing the mouse and click on the tab with this name or clicking on the comments button 1726 as previously described. This section has only one comment field 1802. This should be used to document any comments by the trainer or by the client regarding the following: goals, concerns, medical conditions, any other pertinent information, or trainer comments.

After the user has entered the comments, the user have successfully completed the assessment. The user also has four different options form any of the assessment pages: 1. Print assessments 1804—This will take the user to a form allowing the user to print the client's Initial fitness goals and diet suggestions. 2. New record 1806 This will clear this form and allow the user to enter another member's assessment. 3. Main menu 1808—This will return the user to the Boot/Training sub-Menu, which can take the user back to the Main Menu. 4. Find assessment 1810—this will allow the user to search for a previous assessment.

Final Assessment

The Final Assessment option is used for entering member assessment data at the end of a Initial fitness session, or any time a member is being assessed to without setting goals. This screen is not shown due to the similarity with the initial assessment already described. The final assessment includes the selection of a member, Date, Age, Sex, Assessor and the selection of the use of this assessment as a final assessment. This will make this assessment the final measurements used for comparison for the client. The user should check this box for any ending of Initial fitness assessment. Note: At least one assessment must be selected as a "final" for every member prior to calculating goals. The user will perform the same skin folds measurements and 7-Site Jackson, Pollock and Ward measurements for each of the sites listed. When the user have completed these measurements, the user is finished with the final assessment.

Address Book

Figure 19:
FIG. 19 shows the address Book screen.

The selection to go to the Address Book screen 1900 shown in FIG. 19 is selected with the view address book button 402 shown in FIG. 4. The address book form 1900 displays all of the members (and prospective members) registered in the database. This form shows the following information: member last name 1902, member first name 1904, member ID#1906, membership status 1908, home phone #1910, work phone #1912, and address 1914. The user has the option to click on a series of alphabet letter buttons 1916 to search for members by last name. These buttons allow the user to quickly find any member by last name. The buttons work by clicking on a letter such as (A) to list members a last name beginning with that letter ("A"). This works with any letter selected. Clicking on ALL 1918 will return the to the main listing to include all members. A scroll bar may be presented along the right side of the screen. This helps the user to move down the list of members displayed. Note: No data can be added or changed from this screen. To add or change data, the user must go to the Edit Current Member screen similar to the add member screen shown in FIG. 20. The user may simply click on the close button 1920 to take the user back to the Members Sub-Menu 400.

New/Current Members

The Add New Member option 404 takes the user to a blank member form 2000 (the edit version will have the blanks filled in) shown in FIG. 20 to enter all information on a single member. It is important for the user to check whether or not the member exists before entering them as a new member. Doing so may create multiple records for the same person—making it very difficulty to track important data on the members. The entry fields are as follows:

Member Last Name 2002 and First Name 2004. When the user opens the form 2000, the user will be in the last name box 2002. The user will type in the last name of the member (or prospect) and hit the Tab key to move to next field. The user will then enter the member's first name 2004.

For membership status 2006, the user will check the box for "prospect" if the new addition is only a prospect and is not to be an actual client or member. To check the box 2006, the user will put the mouse on the box 2006 and click once. After checking the box 2006, the user will hit the Tab key to move to the next field. Leaving this field blank indicates that the person is a member. To leave the box blank, the user simply hits the Tab key to move to the next field.

For Member ID 2008, if the person is a current fitness club member, but not in the program database, the user should enter a Barcode ID # assigned to the user. If the person is only a prospect, or not a current member, then the user may use the letter "P" followed by the prospects phone number. The user may then hit the Tab key to move to the next field.

For the Member since field 2010, the user will enter the date when the person became a member of the fitness club. The user can enter the date using the following format "01/01/00" and hit the Tab key to move to the next field.

For the Referred by field 2012, this box will list all current members. The user will select the person's name who referred the member or prospect (if applicable). The user can also leave this box blank if no one referred the new member. Like all lists, the user can begin typing in the first letters of the name the user are looking for, or use the scroll bar to find the name. The user will click once and hit the Tab key to select the name and move to the next field.

For Address 2014, City 2016, State 2018, and Zip Code 2020, the user will enter information into each of these fields and hit the Tab key to move to the next field. The "City" field 2016 and "State" field 2018 will default to the local location unless the user changes them. This is designed to save some time with data entry.

For Home phone 2020 and Work phone 2022, the user will enter the member's phone numbers. The user should enter the area code in addition to the local number. The user do not have to type in the dashes (-) between numbers. When the user is finished, they will hit the Tab key to move to the next field.

For the current training program section 2024, this information should be updated whenever the member changes training programs. The Trainer field 2026 is defaulted to "no trainer". If the member later joins a training program, the user can update this field later. If selected, a list will appear of all trainers. The user may use the scroll bar or begin typing the first name of the trainer to find the correct name, click once on the name and hit the Tab key to select the trainer.

For the training Program 2028, a list will appear of all programs. The user will use the scroll bar to select the program name and click once and hit the Tab key to select the program. Note: This list may longer than the standard 5 Levels of fitness offered. There are different Initial fitness listings for different times (i.e. Initial fitness May 5, 2000 and Initial fitness Aug. 5, 2000). If there is not current listing for the Initial fitness program, the user must return to the Main Menu 102, go to Trainer's Area 108 and select "Add Program" 504 to update the list. If the new member is not currently in a training program, the user will select "None". For Time 2028, a list will appear of times that the member is training. The user may also search for member 2030 to update the records.

When the user is finished, the user has three different options: 1) Begin assessment 2032—This will take the user directly to the new assessment form as previously described. 2) Add new member 2034—This will clear this form and allow the user to enter another member's information following the procedure above. 3) Main Menu 2036—This will return the user to the member sub-menu 400, which can take the user back to the main menu 102.

The Edit current member 406 option takes the user to form showing all the information for a single member. It is the same form that is used for new members, but gives the user access to all current members in the database. For this option, the user may Search for a member 2030 by any of the fields shown. Typically, the user will search for the member by Last Name 2002. A window will appear allowing the user to type in the field the user is searching for. This window allows the user to choose different search options. Select the ones the user want, then click the "find" button. The first record matching the user's search will appear. If this is correct, click the "cancel" button to close the search window and edit the information if appropriate. If this is not correct, the user may click the "find next" button to find another matching record. To Edit Information, the user will use the Tab key to move through the fields to the one the user wish to change or edit. The user can add information to blank fields, or delete current fields and add new information. For specifics on entering information in this form, see the section on "adding a new member". Note: After the user have changed the member information, the user can click on the binocular button again to edit another member's records.

Member Referrals

The Member referrals screen 2100 is shown in FIG. 21. This form 2100 shows all of the prospects 2102 that have been referred by other members. This is to help manage rewards going to current members for referring new members. This list can also be used as a mail merge source into a Microsoft Word™ word processing software document to generate letters to prospects or to the referring members. Note: There is already a standard "prospectives" letter in this database that can be generated for all current clients listed as "prospective".

Trainer Information

Figure 22:
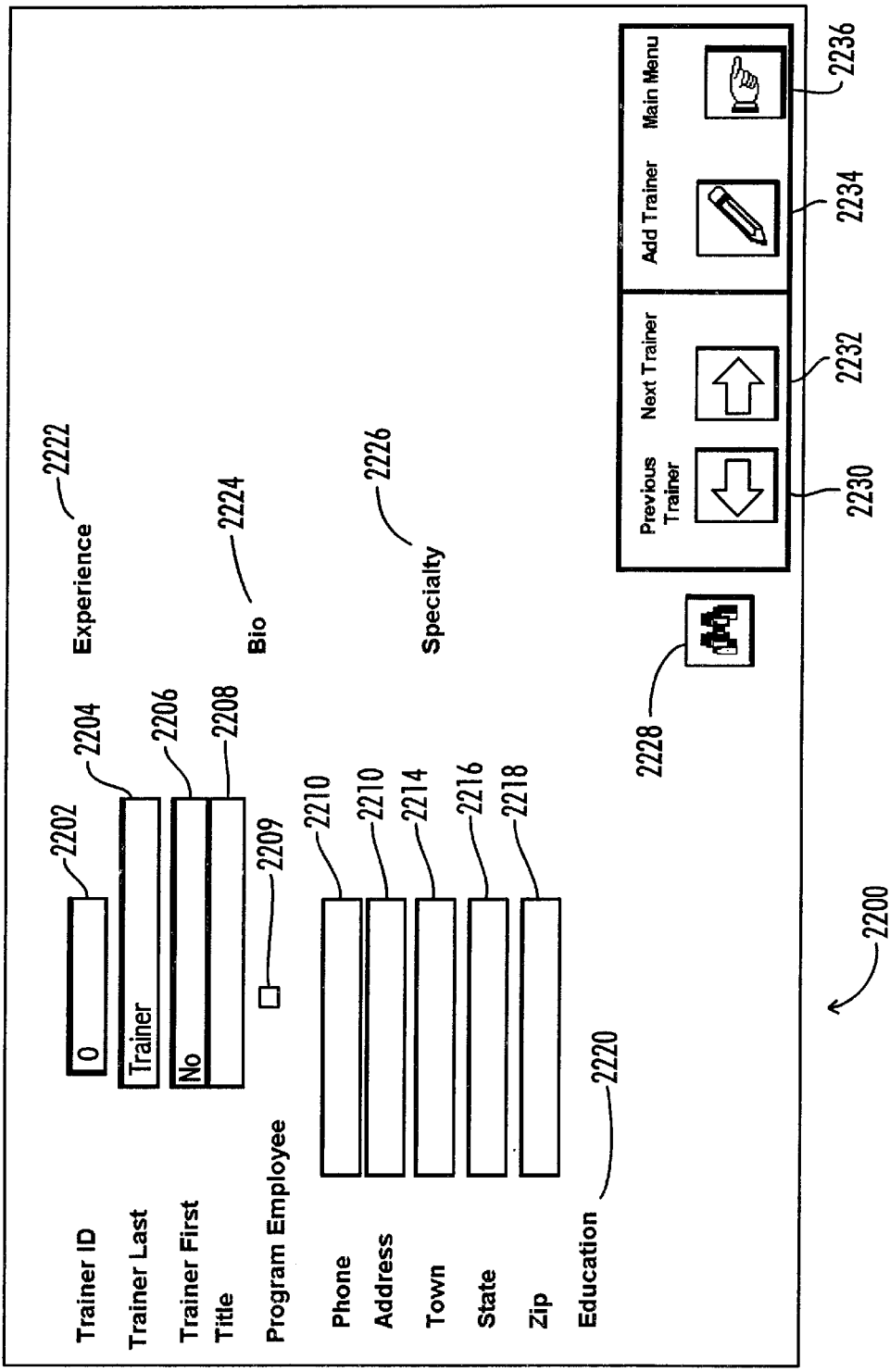
FIG. 22 shows the edit or update trainer information form.

The Edit or update trainer information form 2200 shown in FIG. 22 gives the user the form with the information on a single trainer. The user can search for a Trainer using any of the fields shown 2202, 2204, 2206, 2208, 2210, 2212, 2214, 2216, 2218, 2220, 2222, 2224, 2226. Typically, the user will search for the trainer by Last Name 2204. The user may click on the search button 2228 to locate a trainer and a window will appear allowing the user to type in the name the user is searching for. This window allows the user to choose different search options. The user may select the ones the user wants and then click a find button. The first record matching the user's search will appear. If this is correct, then the user can click the cancel button to close the search window. If this is not correct, then the user can click on the find next button to find another matching record.

Entering data and Editing data uses the following fields.

For Trainer ID 2202, use an assigned number as appropriate for the application. For Trainer Last Name 2204 and First Name 2206, the user will type in the appropriate names of the trainer and hit the Tab key to move to the next field. For Title 2208, the user will type in the employee's title and move to the next field. For Program Employee 2209, the user will check this box depending on the business affiliation of the employee. For education 2220, the user enter the trainer's education. For Phone 2210, the user will enter the trainer's phone number. This is the number that will appear on client paperwork, so make sure it is one the trainer feels comfortable giving out. For Address 2212/City 2214/State 2216/and Zip Code 2218, the user will enter the appropriate information into each of these fields and hit the Tab key to move to the next field. The city field and state field will default to the local area unless the user changes them. Experience 2222 is used for fitness related experience and Specialty 2226 is used with regard to training or specific function as an employee. Bio 2224 may be used for any additional information about the trainer and allows for a large amount of text, if necessary. When the user is finished, the user has several options. Previous Trainer 2230—Clicking on this arrow will move the user to the previous trainer's record. Next Trainer 2232—Clicking on this arrow will move the user to the next trainer's record. Add Trainer 2234—This will clear this form and allow the user to enter another trainer's information following the procedure outlined above. Main Menu 2236—This will return the user to the trainer sub-menu 500, which can take the user back to the main menu 102.

Trainer Schedules

The Trainer schedules form 2300 is shown in FIG. 23. This form can be viewed or printed 508 from the trainer sub-menu 500. No data entry is allowed on this form. This form 2300 shows all trainer-specific information that has been entered into the members database and shows, by trainer 2302, all current clients 2304 arranged by training times 2306 and program 2308. This form also includes the member's phone numbers 2310, 2312, and is a good reference for contacting current clients. All training information should be updated (as needed) in order to keep this information accurate. This information can be updated through the members and trainer information previously discussed.

Assessments by Trainer

The assessments by trainer form 2400 shown in FIG. 24 shows a listing of the assessments for each of the trainers and individual members using the information previously discussed. As shown by the multiple variables which are available on this report, this allow for monitoring of trainer and member performance in a single comprehensive report.

Printing Goals

The Printing goals form 2500 can be accessed from either the New Assessments 1000, 1100, 1200, 1400, 1600, 1700, 1800 or Printing Options 600 Sub-Menus. The user may Choose member and date 2502 by clicking once on this box to display the list of members and assessment dates. A scroll bar may be used to select the member. After selecting the member, the name 2504 and date 2506 will appear in red print below the box. The user should then make sure that this is the assessment the user wants to print, remembering that some members may have more than one assessment. If this is not the correct date 2506, the user may return to the box and select a different date 2506. If it is the correct date, the user is ready to select the report. Clicking on program goals 2508 prints the member's goals for the program. This report includes the body fat and weight loss goals, along with water and cardio targets. Clicking on Meal plan 2510 prints the member's diet plan. There are 12 different plans in the system. One will be selected automatically based on the following information entered during the assessment phase: Workout Time (morning, late morning, afternoon, evening); and Diet Type (35% protein, 30% protein, 26% protein). Each of the diets include 5 meals, broken out as follows: 3 meals are 18% of the total daily calories each; Pre-workout meal is 22% of the total daily calories; and Post-workout meal is 24% of the total daily calories. When the user is finished with this form, they may click on the main menu button 2512 to return to the rest of the system.

Finally, the generate letters form 2600 is shown in FIG. 26. This may be used for generating letters to initial fitness program clients or other members of different training programs. The user first selects 2602, using a scroll list, the programs that they wish to generate letters for, and then clicks the appropriate button 2604, 2606 to send either the standard initial fitness program Welcome Letter or the initial fitness program Meeting Letters. When the user is finished with this form, they may click on the main menu button 2608 to return to the rest of the system.

Thus, although there have been described particular embodiments of the present invention of a new and useful Method and Apparatus for Health and Fitness Feedback, it is not intended that such references be construed as limitations upon the scope of this invention except as set forth in the following claims.

What is claimed is:

1. A method for providing feedback on a member of a fitness program having a body composition and a genetic potential utilizing a computer system database, the method comprising:

performing an initial assessment of the fitness characteristics of a member to gather initial assessment information, including calculating CAMS;

recording the initial assessment information in the computer system database;

performing a final assessment of the fitness characteristics of a member to gather final assessment information, including calculating CAMS;

recording the final assessment information in the computer system database;

calculating the changes in the health characteristics of the member stored in the database between the initial and final assessments.

2. The method of claim 1, the initial and final assessment information comprising diet and cardiovascular characteristics.

3. The method of claim 1, the initial and final assessment information comprising:

a 7-Site Jackson, Pollock and Ward examination on the chest, axilla, triceps, subscapula, abdome, suprailium, and thigh.

4. The method of claim 1, the initial and final assessment information comprising:

tape measurements on the shoulders, chest, waist, hips, upper arm right, upper arm left, thigh right, and thigh left.

5. A method for providing feedback on a member of a fitness program having health characteristics utilizing a computer system database, the method comprising:

monitoring the health characteristics of the member for multiple time intervals, including calculating CAMS;

recording the health characteristics of the member in the database;

selecting two time intervals from the multiple time intervals;

calculating the changes in the health characteristics of the member stored in the database between the two time intervals.

6. The method of claim 5, the health characteristics comprising diet and cardiovascular characteristics.

7. The method of claim 5, the health characteristics comprising:

a 7-Site Jackson, Pollock and Ward examination on the chest, axilla, triceps, subscapula, abdome, suprailium, and thigh.

8. The method of claim 5, the health characteristics comprising:

tape measurements on the shoulders, chest, waist, hips, upper arm right, upper arm left, thigh right, and thigh left.

9. A method for providing feedback on a member of a fitness program having health characteristics utilizing a computer system database, the method comprising:

establishing program goals based on a desired client goal, including calculating CAMS;

recording the program goals of the member in the database;

monitoring the health characteristics of the member for multiple time intervals;

recording the health characteristics of the member in the database;

comparing the health characteristics of the member stored in the database to the program goals stored in the database; and predicting nutritional and exercise quantities require to reach the program goals and the desired client goals.

10. The method of claim 9, wherein establishing program goals includes establishing a target range for a heart rate of the member for a fitness session.

11. The method of claim 9, wherein establishing program goals includes measuring the health characteristics of the member.

12. The method of claim 11, wherein measuring the health characteristics of the member includes collecting diet and cardiovascular characteristics.

13. The method of claim 11, wherein measuring the health characteristics includes a 7-Site Jackson, Pollock and Ward examination on the chest, axilla, triceps, subscapula, abdome, suprailium, and thigh.

14. The method of claim 11, wherein measuring the health characteristics includes taking measurements on the shoulders, chest, waist, hips, upper arm right, upper arm left, thigh right, and thigh left.

15. The method of claim 9, wherein establishing program goals includes selecting a client diet.

16. The method of claim 9, wherein establishing program goals includes predicting fluid loss.

17. The method of claim 9, wherein establishing program goals includes predicting member metabolism by activities performed over a time period.

18. The method of claim 9, wherein establishing program goals includes calculating PAMS.

19. The method of claim 9, wherein establishing program goals includes calculating a cardiovascular requirement for fitness training associated with the desired client goal.

20. A method for providing feedback on a member of a fitness program having a body composition and a genetic potential utilizing a computer system database, the method comprising:

performing an initial assessment of the fitness characteristics of a member to gather initial assessment information, including calculating PAMS;

recording the initial assessment information in the computer system database;

performing a final assessment of the fitness characteristics of a member to gather final assessment information, including calculating PAMS;

recording the final assessment information in the computer system database;

calculating the changes in the health characteristics of the member stored in the database between the initial and final assessments.

21. The method of claim 20, the initial and final assessment information comprising diet and cardiovascular characteristics.

22. The method of claim 20, the initial and final assessment information comprising:

a 7-Site Jackson, Pollock and Ward examination on the chest, axilla, triceps, subscapula, abdome, suprailium, and thigh.

23. The method of claim 20, the initial and final assessment information comprising:

tape measurements on the shoulders, chest, waist, hips, upper arm right, upper arm left, thigh right, and thigh left.

24. A method for providing feedback on a member of a fitness program having health characteristics utilizing a computer system database, the method comprising:

monitoring the health characteristics of the member for multiple time intervals, including calculating PAMS;

recording the health characteristics of the member in the database;

selecting two time intervals from the multiple time intervals;

calculating the changes in the health characteristics of the member stored in the database between the two time intervals.

25. The method of claim 24, the health characteristics comprising diet and cardiovascular characteristics.

26. The method of claim 24, the health characteristics comprising:

a 7-Site Jackson, Pollock and Ward examination on the chest, axilla, triceps, subscapula, abdome, suprailium, and thigh.

27. The method of claim 24, the initial and final assessment information comprising:

tape measurements on the shoulders, chest, waist, hips, upper arm right, upper arm left, thigh right, and thigh left.

28. A method for providing feedback on a member of a fitness program utilizing a computer system database, the method comprising:

establishing program goals based on a desired client goal, including calculating PAMS;

recording the program goals of the member in the database;

monitoring the health characteristics of the member for multiple time intervals;

recording the health characteristics of the member in the database; and comparing the health characteristics of the member stored in the database to the program goals stored in the database.

29. The method of claim 28, wherein establishing program goals includes establishing a target range for a heart rate of the member for a fitness session.

30. The method of claim 28, wherein establishing program goals includes measuring the health characteristics of the member.

31. The method of claim 30, wherein measuring the health characteristic of the member includes collecting diet and cardiovascular characteristics.

32. The method of claim 30, wherein measuring the health characteristics includes a 7-Site Jackson, Pollock and Ward examination on the chest, axilla, triceps, subscapula, abdome, suprailium, and thigh.

33. The method of claim 30, wherein measuring the health characteristics includes taking measurements on the shoulders, chest, waist, hips, upper arm right, upper arm left, thigh right, and thigh left.

34. The method of claim 28, wherein establishing program goals includes selecting a client diet.

35. The method of claim 28, wherein establishing program goal includes predicting fluid loss.

36. The method of claim 28, wherein establishing program goals includes predicting member metabolism by activities performed over a time period.

37. The method of claim 28, wherein establishing program goals includes calculating CAMS.

38. The method Of claim 28, wherein establishing program goals includes calculating a cardiovascular requirement for fitness training associated with the client goals.

* * * * *